US007797109B2

(12) United States Patent
Kirkpatrick et al.

(10) Patent No.: US 7,797,109 B2
(45) Date of Patent: Sep. 14, 2010

(54) METHOD FOR DETERMINING AND REPORTING THE PRESENCE OF RED TIDE AT BEACHES

(75) Inventors: Barbara A. Kirkpatrick, Sarasota, FL (US); Robert D. Currier, Clarksville, VA (US)

(73) Assignee: Mote Marine Laboratory, Sarasota, FL (US)

( * ) Notice: Subject to any disclaimer, the term of this patent is extended or adjusted under 35 U.S.C. 154(b) by 0 days.

(21) Appl. No.: 11/742,010

(22) Filed: Apr. 30, 2007

(65) Prior Publication Data

US 2008/0270029 A1 Oct. 30, 2008

(51) Int. Cl.
*G01W 1/00* (2006.01)
*G06F 19/00* (2006.01)

(52) U.S. Cl. ............................ 702/3; 702/2; 73/170.29

(58) Field of Classification Search .................... 702/2, 702/3, 4, 5
See application file for complete search history.

(56) References Cited

U.S. PATENT DOCUMENTS

| | | | | |
|---|---|---|---|---|
| 6,023,223 | A * | 2/2000 | Baxter, Jr. ................... 340/531 |
| 6,498,987 | B1 * | 12/2002 | Kelly et al. ..................... 702/3 |
| 6,542,825 | B2 * | 4/2003 | Jones et al. ..................... 702/3 |
| 6,553,336 | B1 * | 4/2003 | Johnson et al. ............... 702/188 |
| 6,574,561 | B2 * | 6/2003 | Alexander et al. .............. 702/5 |
| 6,771,969 | B1 * | 8/2004 | Chinoy et al. .............. 455/456.1 |
| 6,816,878 | B1 * | 11/2004 | Zimmers et al. ............. 709/200 |
| 6,823,263 | B1 * | 11/2004 | Kelly et al. ..................... 702/3 |
| 6,999,876 | B2 * | 2/2006 | Lambert et al. ................. 702/2 |
| 7,027,808 | B2 * | 4/2006 | Wesby ........................ 455/419 |
| 7,181,345 | B2 * | 2/2007 | Rosenfeld et al. .............. 702/3 |
| 2002/0042846 | A1 * | 4/2002 | Bottan et al. ................ 709/249 |
| 2002/0059030 | A1 * | 5/2002 | Otworth et al. ............... 702/19 |
| 2004/0006513 | A1 * | 1/2004 | Wolfe .......................... 705/22 |
| 2005/0006316 | A1 * | 1/2005 | Cushman et al. ............. 210/760 |
| 2005/0031198 | A1 * | 2/2005 | Perrier ........................ 382/157 |
| 2005/0222933 | A1 * | 10/2005 | Wesby ......................... 705/36 |
| 2005/0271266 | A1 * | 12/2005 | Perrier ........................ 382/157 |
| 2007/0111243 | A1 * | 5/2007 | Paul ............................... 435/6 |

OTHER PUBLICATIONS

B. Kirkpatrick et al., "Literature review of Florida red tide: implications for human health effects", Harmful Algae 3 (2):99-115 (2004).
L. E. Fleming et al., "Initial evaluation of the effects of aerosolized Florida red tide toxins (brevetoxins) in persons with asthma", Environ Health Perspect 113(5):650-657 (2005).

(Continued)

*Primary Examiner*—Hal D Wachsman
(74) *Attorney, Agent, or Firm*—IPLM Group, P.A.

(57) ABSTRACT

Human observers stationed on or near beaches gather subjective observations of one or more observable beach conditions associated with respiratory distress. Subjectively determined observations such as dead fish and audible coughing provide a better indication of the likelihood of respiratory distress than measurements made using scientific instruments. The observations may be sent to a remote central database using handheld communication devices. A beach status evaluation is determined based on stored observations, and may be provided to beachgoers through Internet web pages or by telephone or text-message to enable beachgoers to choose an alternative beach or alternative activity when respiratory distress is likely.

17 Claims, 2 Drawing Sheets

OTHER PUBLICATIONS

L. E. Fleming et al., "Aerosolized Red-Tide Toxins (Brevetoxins) and Asthma", Chest Journal, 131(1):187-194, Jan. 2007.

Cheng, Yung Sung et al., Characterization of Marine Aerosol for Assessment of Human Exposure to Brevetoxins, Environmental Health Perspectives, vol. 113, No. 5, May 2005, pp. 638-643.

Beach Conditions Reporting System for the Gulf Coast of Florida™ for the Florida Panhandle, obtained from http://coolgate.mote.org/beachconditions/, 1 page, Sep. 30, 2009.

Beach Conditions Reporting System for the Gulf Coast of Florida™ for the Florida Panhandle and beach locations in Okaloosa County, obtained from http://coolgate.mote.org/beachcondiions/, 1 page, Sep. 30, 2009.

Beach Conditions Reporting System for the Gulf Coast of Florida™ for the Southwest Coast of Florida, obtained from http://coolgate.mote.org/beachconditions/, 1 page, Sep. 30, 2009.

Beach Conditions Reporting System for the Gulf Coast of Florida™ for the Southwest Coast of Florida and beach locations in Collier County, obtained from http://coolgate.mote.org/beachconditions/, 1 page, Sep. 30, 2009.

Music, Stanley I. et al., "*Red Tide Its Public Health Implications*", J. Florida M.A., vol. 60, 11, pp. 27-29, Nov. 1973.

* cited by examiner

METHOD FOR DETERMINING AND REPORTING THE PRESENCE OF RED TIDE AT BEACHES

FIELD

The present invention relates to methods for reporting red tide blooms.

BACKGROUND

Florida red tides occur annually in the Gulf of Mexico from blooms of the marine dinoflagellate *Karenia brevis* (*K. brevis*). These blooms (also known as harmful algal blooms or HABs) can cause massive fish kills, mortality to marine mammals and other sea life, and production of polycyclic ethers collectively termed "brevetoxins". Human exposure to brevetoxins produced by *K. brevis* occurs through two routes, either through eating contaminated shellfish, or through inhaling airborne toxin, see e.g., B. Kirkpatrick et al., "Literature review of Florida red tide: implications for human health effects", *Harmful Algae* 3(2):99-115 (2004). Current human exposure to brevetoxins through eating contaminated shellfish is well-controlled through closure of shellfish beds during toxic algal blooms. However, respiratory effects experienced by persons inhaling airborne toxin on beaches and in coastal communities remain a significant concern. Brevetoxins cause respiratory problems in those living near the beach, in recreational beachgoers, and in occupationally exposed persons, with unknown long-term effects. The accompanying respiratory discomfort may significantly impact personal health, particularly for those already compromised with asthma, allergies, chronic obstructive pulmonary disease or other conditions, see e.g., L. E. Fleming et al., "Initial evaluation of the effects of aerosolized Florida red tide toxins (brevetoxins) in persons with asthma", *Environ Health Perspect* 113(5):650-657 (2005). Respiratory discomfort may also have a significant impact on area tourism by greatly limiting recreational beach enjoyment.

Current efforts focus on mitigation of red tide blooms, but with limited success. In the absence of immediate mitigation, it is necessary to minimize effects of red tide blooms as much as possible, particularly when health concerns are involved. Systems to provide objectively measured data concerning red tide toxins in specific areas currently exist, such as call-in hotlines, websites, and periodic bulletin services that provide objective, scientifically measured data regarding bloom status and algal concentrations.

SUMMARY OF THE INVENTION

The services and objective data provided by these services have many limitations. Among these limitations are delays in and the general nature of the data and an inability to assess subjective conditions such as comfort levels at the beach. Call-in hotlines and websites provide information based on measured cell counts in certain areas. These data are typically only updated on a weekly basis. A periodic bulletin service from the National Oceanic and Atmospheric Administration (NOAA) provides reports of blooms in the southwestern coast of Florida but is not specific for particular recreational beaches. The NOAA bulletins are based on chlorophyll data assimilated from satellite imagery supplemented by cell count data from shoreline sampling or seaborne gliders collected a few days prior to the bulletin release. Although NOAA bulletins can be quite helpful, they are limited in frequency, do not provide real-time or near-real-time information, are not location-specific, and do not address symptoms actually experienced by beachgoers.

As atmospheric and oceanic conditions changes, algal blooms change as well. Blooms are patchy and dynamic, and can change in size and location during the course of a day, leading to a bloom causing respiratory effects on a particular beach one day, but with more limited respiratory effects being experienced the next day. Similarly, a beach at which no respiratory distress symptoms are noticed one day may exhibit significant distress symptoms the next day. Cell counts, wind speed, and wind direction are not adequate predictors of human discomfort associated with red tide toxins. For example, cell counts and discomfort levels are poorly correlated. Current scientific methods for measuring airborne toxin levels are not sensitive enough to detect toxin levels that can induce respiratory symptoms in humans. The current limit of detection for existing air monitor technology is about 0.2 ng/m$^3$. Many people experience respiratory distress symptoms at toxin levels apparently below this detection limit. Thus even when the prevailing winds are off-shore and toxins are below detectable levels, respiratory discomfort may be experienced.

Because inhaled brevetoxins can compromise the health of beachgoers, a system that provides more frequent, more timely, or more sensitive reporting on beach conditions is needed. A warning system desirably would also inform people (e.g., residents and tourists) of red tide or respiratory distress levels at specific beaches so that the affected beaches could be avoided or different beaches or alternate recreation could be chosen. A warning system desirably would enable sensitive individuals to avoid the beach entirely on certain days, or to select a beach with less intense red tide toxin effects.

The present invention utilizes subjective monitoring of beach conditions using one or more and desirably a plurality of human observers stationed on or near area beaches. The system employs data subjectively gathered by the observer(s) concerning the frequency of coughing or other observable respiratory distress indicators, or other observable conditions (e.g., fish kills, water color or wind speed and direction) that may be associated with respiratory distress. The gathered data desirably includes at least one observable condition for which subjectively-gathered data is a more sensitive indicator of red tide-related respiratory distress than data gathered via airborne monitoring. The gathered data is transferred from the observer(s) to the general public using a communication system and a database. The system desirably monitors a plurality of beaches so that users can compare conditions among them. The system may also monitor wind, wave, and other conditions that might appeal to other beachgoer categories, such as surfers or the parents of young children. The system may also monitor or warn of adverse conditions other than red tide, such as weather events including storms, tornadoes and tsunamis, and sealife dangers including jellyfish, sharks and stingrays.

The invention thus provides, in one aspect, a method for making beach status information available to a person who wishes to visit a beach, the method comprising the steps of:
 a) obtaining from a human observer stationed on or near a beach subjective observations of one or more observable beach conditions associated with respiratory distress;
 b) storing the observations in a database;
 c) determining a beach status evaluation based on a plurality of the observations; and
 d) providing such beach status evaluation to the person.

In a preferred aspect, the beach status evaluation is indicative of red tide, or the likelihood of respiratory distress due to red tide, at one or more specific beaches. In another preferred aspect, the observable beach condition comprises one or more of: audible evidence of respiratory irritation, visible evidence of respiratory irritation, visible dead fish, water color or wind direction. In a further preferred aspect, the observations are recorded, stored or transmitted to a remote database using handheld personal communications devices such as mobile telephones, wireless e-mail devices, wireless personal digital assistants or portable computers equipped with wireless access. In yet another preferred aspect, beach status evaluations are sent to users via such personal communications devices or via other electronic communications services such as the Internet, automated telephone messages or text messages.

BRIEF DESCRIPTION OF THE DRAWING

The present invention will be better understood by way of the specific embodiments shown in the following figures, the purpose of which are to illustrate the invention rather than to limit its scope.

Like reference symbols in the various figures of the drawing indicate like elements. The elements in the drawing are not to scale.

DETAILED DESCRIPTION

The terms "a," "an," "the," "at least one," and "one or more" are used interchangeably.

The recitation of numerical ranges by endpoints includes all numbers subsumed within that range (e.g., 1 to 5 includes 1, 1.5, 2, 2.75, 3, 3.80, 4, 5, etc.).

The term "comprises" and variations thereof does not have a limiting meaning where such term appears in the description or claims. For example, a method comprising an observation step may include additional unnamed observations steps.

The terms "preferred" and "preferably" refer to embodiments that may afford certain benefits, under certain circumstances. However, other embodiments may also be preferred, under the same or other circumstances. The recitation of one or more preferred embodiments does not imply that other embodiments are not useful, and is not intended to exclude other embodiments from the scope of the invention.

Figure 1:
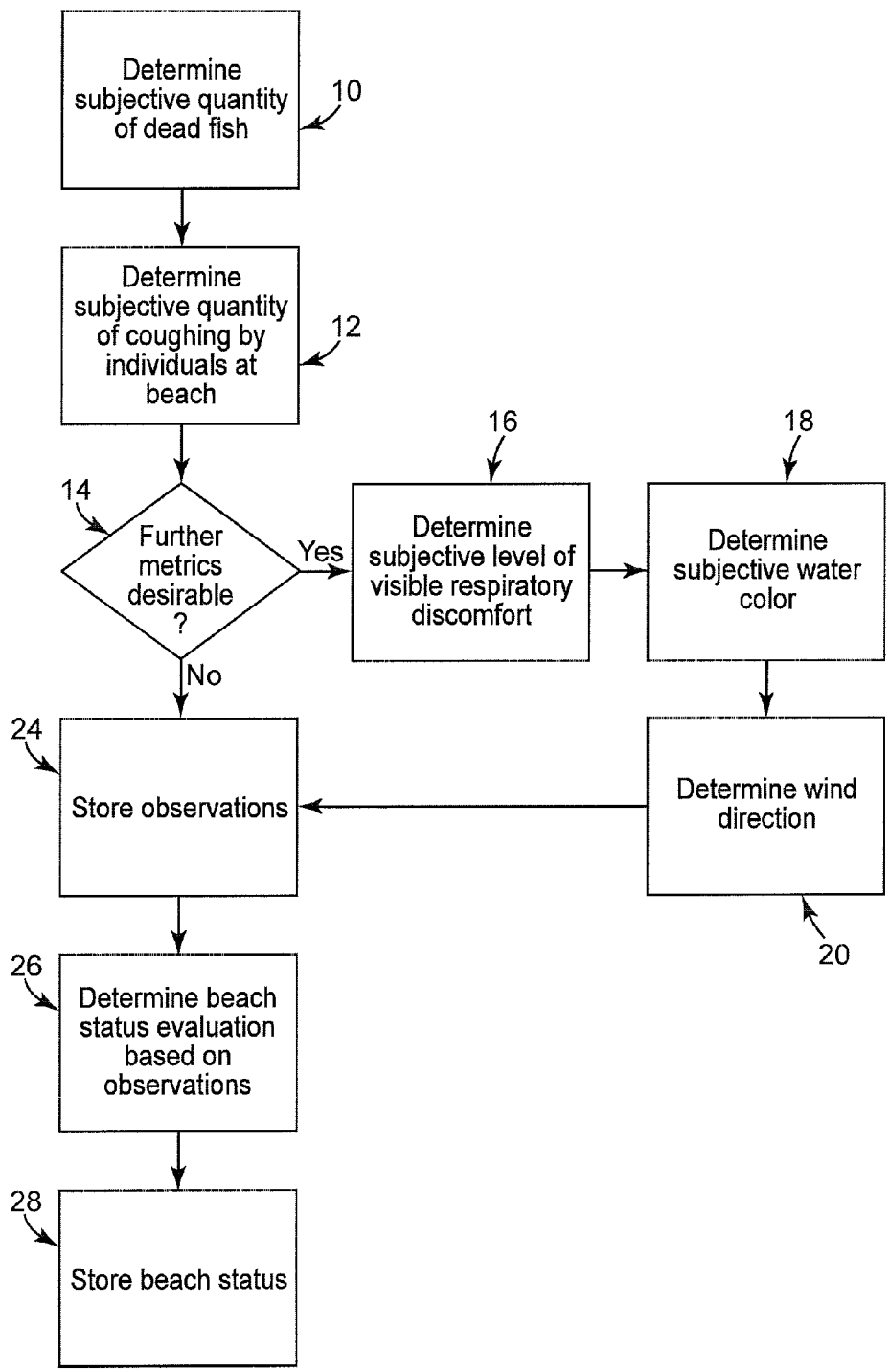
FIG. 1 is a flowchart for determining and storing subjective beach observations.

FIG. 1 depicts an exemplary method for obtaining and storing subjective observations indicative of the existence and severity of red tide at a beach. At periodic intervals human observers (e.g., lifeguards, parks and recreation personnel, concessionaires or other government or business employees, owners or operators, or volunteers) stationed on or near the beach subjectively evaluate various criteria. The chosen times and intervals may vary and may for example involve at least 2, at least 3, at least 4 or at least 5 observations per day, at regular or altered intervals such as 1, 2, 3, 4, 5 or more hours between observations. Observations may be targeted to accommodate possible peak request times from users for beach status information, and for example may involve observations taken at 6:00 A.M., 10:00 A.M. and 3:00 P.M. local time. These hours may correspond to public requests concerning early morning or after-work walks or runs on the beach, or to beach personnel scheduling such as the arrival of lifeguards at the start of the day or at a shift change. The observations may be taken in a variety of ways and may optionally employ instrumentation such as stopwatches, anemometers, wind vanes, thermometers and the like. Desirably however the amount of such instrumentation will be kept to a minimum so as to increase the likelihood that observations will be regularly obtained and stored. The observations may be obtained at fixed or varied vantage points, and desirably are repeatedly obtained from fixed locations.

The chosen observation criteria may also vary. For example, the observer may scan the selected beach from a vantage point and determine 10 a subjective quantity of dead fish visible on the beach. This may be recorded using an approximate rating (e.g., "none", "few" or "many") or a count based on selected ranges (e.g., "less than 5", "6 to 25" or "more than 26"). These quantities may be based on prior experience at the selected beach. For example, a lifeguard working at a beach which typically exhibits large numbers of beached dead fish may need to see relatively more dead fish before selecting "many" than a lifeguard working at a beach which seldom exhibits beached dead fish.

The beach personnel may also determine 12 subjective audible evidence of coughing by beachgoers. The number of coughs heard within a given span of time appears to be a much more accurate indicator of red tide events than measurements obtained using scientific instrumentation. Coughing may be monitored in a number of ways. For example, the observer may go to a selected vantage point and listen for coughing for several seconds, with eyes closed. This may be recorded using an approximate rating (e.g., "none", "few" or "many") or a count based on selected ranges in a selected span of time (e.g., "none", "1 to 5 per minute", "6 to 30 per minute" or "more than 30 per minute"). The observer may also or instead base the audible respiratory irritation observation on the observer's own subjective respiratory condition.

The quantity of dead fish and audible coughing are primary factors for determining the existence of red tide. However, if other factors are available, the observers may determine 14 to obtain observations for such other factors as well. For example, the observers may determine 16 subjective visual evidence of respiratory irritation by beachgoers. Visible signs of such distress may include wheezing, sneezing, coughing, asthma or the use of inhalers, or other visible forms of discomfort. The observers may also or instead determine 18 the subjective water color, noting for example whether the color is "clear", "moderately reddened" or "dark brownish-red". The observers may also or instead determine 20 the wind direction, noting for example the prevailing winds in terms of one of the four cardinal directions.

The observers may record their observations in a suitable paper ledger (e.g., a notebook) or directly enter the observations into an appropriate personal communications device (e.g., a mobile telephone, personal data assistant or portable computer equipped with wireless access) so the observations may immediately or soon thereafter be sent to and stored 24 in a database. The observations may be recorded or sent in a variety of ways including the use of telephone touchpad keys, custom-made software or Internet-based website forms. A plurality of the observations are then compared to appropriate selection criteria to determine 26 a beach status evaluation (e.g., whether a red tide event is taking place) at the selected beach. The selection criteria may be experimentally determined using algorithms, statistical models or other methodologies that will be apparent to persons skilled in the art. The selection criteria may be fixed or continually updated. The beach evaluation may take a variety of forms, e.g., a respiratory distress indication or red tide condition such as "none", "low", "moderate", or "high". The beach evaluation may be stored 28 so that it may be sent to users until such time as a new beach evaluation is available, or it may be redetermined each time a request for beach status information is received. Once stored, beach status evaluations may be made available to individuals via access tailored to the particular medium in which the beach status evaluation is stored. Beach status evaluations may for example be stored in an electronic database server accessible via the Internet, via inbound telephonic inquiry, via outbound recorded telephone messages or via outbound text messages. Beach status evaluations may for example be displayed in a map format showing the public beaches in an area (e.g., a city or county) and the conditions at each beach. To avoid misinterpretation of data, old reports (e.g., reports older than 8 hours or older than 24 hours) may be deleted from the reporting system. If an updated beach status evaluation is not available, a message such as "no report" or other appropriate guidance may be given.

Figure 2:
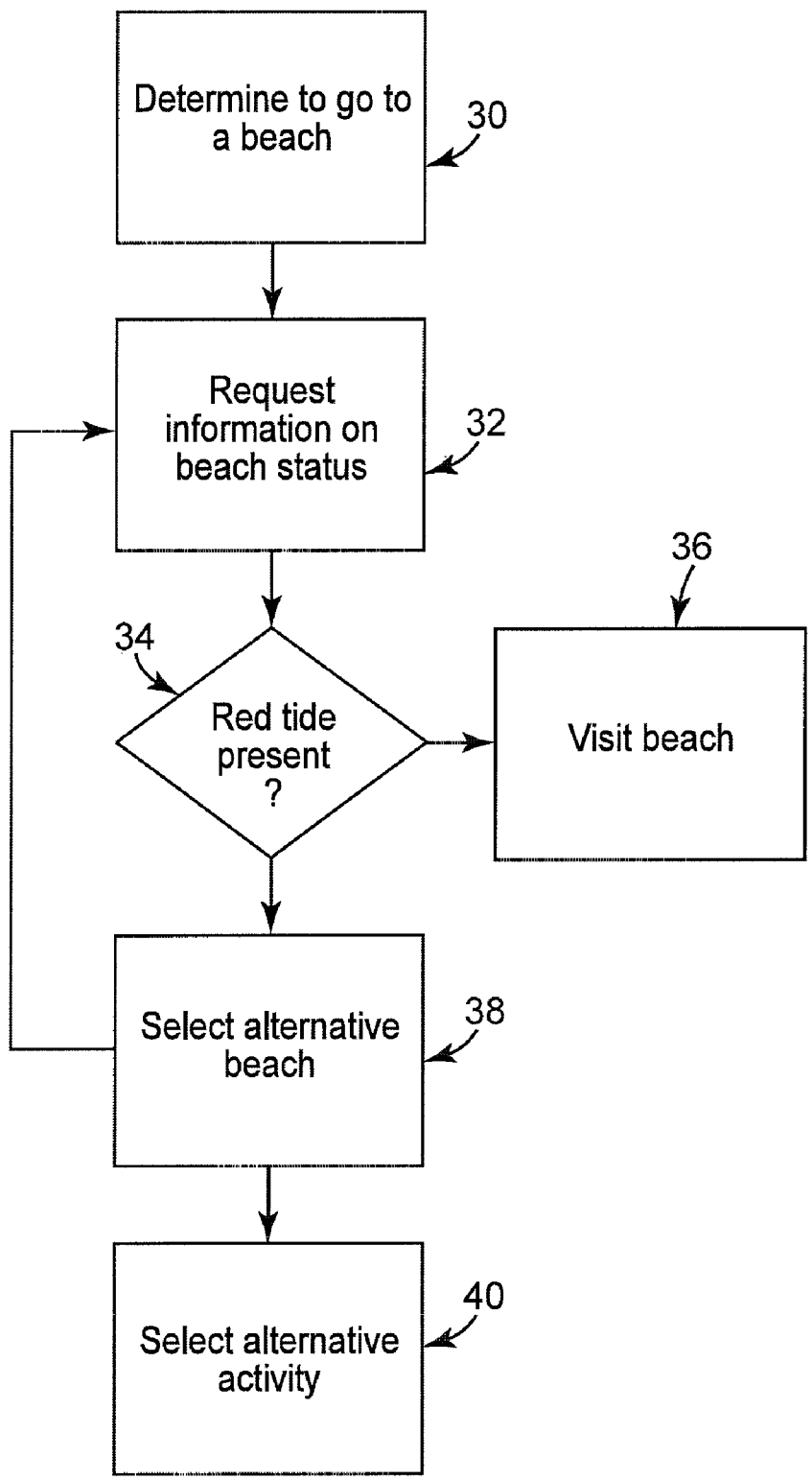
FIG. 2 is a flowchart for utilizing the subjective beach status to determine a beach to attend.

FIG. 2 describes one mechanism by which beach patrons may select a beach so as to avoid red tide. Once a prospective beach patron has decided 30 to visit a beach, the prospective patron may request 32 information concerning the selected beach. For example, the patron may go to a website and look up the beach status evaluation for the selected beach. A patron may also or instead send an e-mail message to a server which would transmit an automated reply containing information concerning the selected beach and other beaches in the vicinity of the selected beach. The patron may also or instead send a text message to a particular number which would reply with an automated response. The patron may also or instead call a telephone number, where an automated menu system may step the patron through a menu to ultimately arrive at the desired beach status evaluation.

Based on the information obtained, the prospective patron determines 34 whether the degree of red tide present at the selected beach is within allowable limits, and thus visit 36 the selected beach with increased confidence that the patron will not experience respiratory distress, or if the severity of red tide present is unacceptable may select 38 an alternative beach and repeat the steps described above to determine whether the severity of red tide at the newly selected beach is within acceptable limits. The user may (e.g., when conditions are unfavorable at all convenient beaches) select 40 an alternative activity such as an alternative recreational activity. Users may be asked to report their own experience following a visit to determine if a beach status evaluation was deemed accurate by users who relied upon it.

It is desirable to shorten where possible the time lag between observation of a beach condition and the availability of an updated beach status evaluation. For example, time frames as short as one hour or less, 30 minutes or less, or 15 minutes or less may be sufficient for observers to note conditions corresponding to a red tide outbreak and for a corresponding beach status evaluation to be made available to prospective beachgoers. The disclosed method is especially useful in areas with a plurality of beaches. By providing up-to-date beach status evaluations for a variety of beaches in an area, the system may enable users to choose an appropriate beach while minimizing travel times and distances. The disclosed method may be employed in large areas such as beaches throughout a state or throughout a plurality of states. The method allows end-users to determine whether or not to go to a particular beach on a particular day based on the likelihood of encountering respiratory distress such as may be caused by red tide. When available for a plurality of beaches, the disclosed method can allow an end-user to determine which of those beaches is least likely to be impacted by red tide. The disclosed method may provide updates to current beach conditions several times a day and thereby can provide more timely and more accurate indications of the likelihood of respiratory distress conditions at one or more individual beaches.

In additional embodiments, the disclosed method may provide an early warning for other benign or adverse conditions at one or preferably a plurality of beaches. Exemplary such conditions include severe weather (e.g., storms, tornadoes or tsunamis), approaching storm systems, cloud patterns, wave action, sealife migration patterns (e.g., birds, whales or dolphins) or the presence of potentially harmful sealife (e.g., jellyfish, sharks or stingrays).

The invention is further illustrated in the following illustrative example.

EXAMPLE

An Internet-based beach reporting system was assembled using open source tools, namely a Tool Command Language described at tcl.tk, a database engine described at sqlite.org, a scripting language described at php.net, an Asynchronous JavaScript and XML interactive web page (AJAX) hosting system described a en.wikipedia.org/wiki/Ajax(programming), a SQL database library described at mysql.com, an interactive voice response system described at alpha.greenie.net/vgetty, a text-to-speech system described at cepstral.com and a map-building application described at maps.google.com. The system was hosted on a server at Mote Marine Laboratory's Sarasota Operations Coastal Ocean Observation Laboratory in Sarasota, Fla. Lifeguards at 6 public beaches in Sarasota County (ranging from Lido Key near Sarasota, Fla. to Manasota Beach near South Venice Fla.) and later 2 additional public beaches in Manatee County (Manatee Beach and Coquina Beach) were equipped with BLACK-BERRY™ wireless devices from Research in Motion, Inc, and asked to provide periodic subjective daily observations at 6:00 A.M., 10:00 A.M. and 3:00 P.M. Using the BLACK-BERRY devices, the lifeguards sent to the server their subjective ratings of dead fish counts, audible coughing, water color, wind direction, surf conditions and the color of the beach flag (green flag—good swimming conditions; yellow flag—use caution; red flag—dangerous swimming conditions; double red flag—beach is closed to swimming; purple flag—hazardous marine life). Beach status evaluations were made available via the Internet at coolgate.mote.org/redtide/ and later at coolgate.mote.org/beachconditions. Beach status evaluations were also made available via an interactive voice response phone tree. Beach evaluations were date and time stamped so that users could determine how recently the evaluation was made.

Various modifications and alterations of this invention will be apparent to those skilled in the art without departing from this invention. This invention should not be restricted to that which has been set forth herein only for illustrative purposes.

What is claimed is:

1. A method for making beach status information available to a person who wishes to visit a beach, the method comprising the steps of:
 a) storing by a host computer system data gathered by human observers stationed on or near a beach concerning the frequency of coughing or other observable respiratory distress indicators by beachgoers, including at least one observable condition for which subjectively-gathered data is a more sensitive, more timely or more accurate indicator of red tide-related respiratory distress than data gathered via airborne monitoring and scientific instrumentation;

b) a determining by a host computer system a current or timely beach status evaluation based on the stored subjectively-gathered data; and c) transmitting by a host computer system such beach status evaluation to such person before that person visits the beach.

2. The method of claim 1 wherein the host computer system stores data concerning a quantity of dead fish visible on the beach.

3. The method of claim 1 wherein the host computer system stores data concerning audible evidence of coughing by beachgoers.

4. The method of claim 1 wherein the host computer system stores data concerning visual evidence of respiratory irritation by beachgoers.

5. The method of claim 1 wherein the host computer system stores data concerning water color.

6. The method of claim 1 wherein the host computer system stores data concerning wind direction.

7. The method of claim 1, wherein the host computer system stores data concerning severe weather, approaching storm systems, cloud patterns, wave actions, sealife migration patterns or the presence of potentially harmful sealife.

8. The method of claim 1 wherein the beach status evaluation is indicative of red tide.

9. The method of claim 1 further comprising sending the gathered data to a host computer system via a handheld personal communications device.

10. The method of claim 9 wherein the personal communications device comprises a mobile telephone, wireless e-mail device, wireless personal digital assistant or portable computer equipped with wireless access.

11. The method of claim 1 comprising providing the beach status evaluation to such person via a personal communications device.

12. The method of claim 11 wherein the personal communications device comprises a mobile telephone, wireless e-mail device, wireless personal digital assistant or portable computer equipped with wireless access.

13. The method of claim 1 comprising providing beach status evaluations via a website.

14. The method of claim 1 comprising providing beach status evaluations via e-mail.

15. The method of claim 1 comprising providing beach status evaluations via text messages.

16. The method of claim 1 comprising providing beach status evaluations via telephone.

17. The method of claim 1 comprising providing beach status evaluations for each of a plurality of beaches.

* * * * *